(12) United States Patent
Conroy

(10) Patent No.: US 11,133,110 B2
(45) Date of Patent: Sep. 28, 2021

(54) SYSTEMS AND METHODS FOR ASSESSING WHETHER MEDICAL PROCEDURES SHOULD BE APPROVED

(71) Applicant: Mark Conroy, The Woodlands, TX (US)

(72) Inventor: Mark Conroy, The Woodlands, TX (US)

(73) Assignee: HealthHelp, LLC, Wilmington City, DE (US)

( * ) Notice: Subject to any disclaimer, the term of this patent is extended or adjusted under 35 U.S.C. 154(b) by 0 days.

(21) Appl. No.: 16/236,262

(22) Filed: Dec. 28, 2018

(65) Prior Publication Data

US 2019/0392950 A1  Dec. 26, 2019

Related U.S. Application Data

(60) Provisional application No. 62/687,906, filed on Jun. 21, 2018.

(51) Int. Cl.
| | |
|---|---|
| *G16H 50/20* | (2018.01) |
| *G16H 10/60* | (2018.01) |
| *G06N 3/02* | (2006.01) |

(52) U.S. Cl.
CPC ............... *G16H 50/20* (2018.01); *G06N 3/02* (2013.01); *G16H 10/60* (2018.01)

(58) Field of Classification Search
CPC ........... G16H 50/20; G16H 10/60; G06N 3/02
USPC .......................................... 707/736; 705/2, 3
See application file for complete search history.

(56) References Cited

U.S. PATENT DOCUMENTS

| | | | |
|---|---|---|---|
| 2004/0044546 A1* | 3/2004 | Moore | G06F 19/325 705/2 |
| 2005/0075904 A1* | 4/2005 | Wager | G06Q 10/10 705/2 |
| 2009/0319518 A1* | 12/2009 | Koudas | G06F 16/951 |
| 2013/0239006 A1* | 9/2013 | Tolkachev | G06N 3/02 715/738 |
| 2017/0285584 A1* | 10/2017 | Nakagawa | B25J 9/1671 |
| 2017/0344550 A1* | 11/2017 | Fischer | G06F 16/24578 |

* cited by examiner

*Primary Examiner* — Hares Jami
(74) *Attorney, Agent, or Firm* — Kelley Drye & Warren LLP

(57) ABSTRACT

A rules engine that allows constructing and processing rules within a software application using protocol driven processing. A machine learning algorithm may be used to assess requested procedures that are initially rejected. The machine learning algorithm may also be saved periodically or at the time of each assessment and accessed at a later time.

20 Claims, 13 Drawing Sheets

Add Rule: Breast Cancer Screening » Breast Cancer Screening » Asymptomatic High Risk Patient Action: Select Action
Queue: Select Queue
Next Protocol: Select Next Protocol
Next Node: Select Next Node
Confidence: 100
Title:
Note: $RID'S $ACTIONCODE$ $CRITDESC$ $CRIT$ $RTITLE$
Label:

Update

| Modality Code | Description | Action |
|---|---|---|
| MRA | MAGNETIC RESONANCE ANGIOGRAPHY, HEAD, WITHOUT CONTRAST MATERIAL(S) | Proceed to complete |
| MRA | MAGNETIC RESONANCE ANGIOGRAPHY, HEAD, WITH CONTRAST MATERIAL(S) | Proceed to complete |
| MRA | MAGNETIC RESONANCE ANGIOGRAPHY, HEAD, WITHOUT CONTRAST MATERIAL(S), FOLLOWED BY CONTRAST MATERIAL(S) AND FURTHER SEQUENCES | Proceed to complete |
| | COMPUTED TOMOGRAPHY, HEAD OR BRAIN, WITH CONTRAST MATERIAL(S) | Request clinical consultation |
| | No imaging | Proceed to complete |

FIG. 13

SYSTEMS AND METHODS FOR ASSESSING WHETHER MEDICAL PROCEDURES SHOULD BE APPROVED

CROSS-REFERENCE TO RELATED APPLICATION

This application claims the benefit of U.S. Provisional Patent Application No. 62/687,906, filed Jun. 21, 2018, the entire contents of which are incorporated herein by reference.

BACKGROUND OF THE INVENTION

In 2016, U.S. health care costs were over $3 trillion. That amounted to approximately 18 percent of gross domestic product. In comparison, in 1960, health care cost were approximately $27 billion, just 5 percent of GDP.

The price of medical care is the largest factor driving U.S. healthcare costs, accounting for approximately 90% of spending. These expenditures include the cost of caring for those with chronic or long-term medical conditions, an aging population, and the increased cost of new medicines, procedures and technologies. Also, recent healthcare reform law has expanded access to insurance to millions of Americans. The U.S. has transitioned to a healthcare system in which everyone can obtain health insurance regardless of age or health status, and many individuals who are newly insured need ongoing medical attention.

To prevent health insurance costs from spiraling out of control, insurance companies have instituted various cost-containment procedures. Common cost-containment procedures, under which coverage may be restricted, include: pre-admission testing (additional testing performed to determine whether hospitalization or surgery is required in non-emergency situations); second opinions (a second opinion from a health care practitioner may be required before treatment is authorized); prior consent for hospitalization (an insurance company must pre-authorize a proposed treatment); and limitation of health care procedures, services and related expenditures outside the usual, customary and reasonable charges for particular courses of care. However, most of these cost-containment procedures can delay treatment and increase the time expended by medical professional on each patient.

Software solutions may be implemented to reduce the time needed for submission, review, and approval of procedure requests. Providers may submit patient clinical criteria and/or procedure requests via a software solution. If the information provided about a proposed procedure or test meets evidence-based criteria, the software may automatically return an indication that the procedure or test is approved. Providers may also be presented with alternatives to the originally requested test or procedure.

If the treatment falls outside of pre-set clinical guidelines, or if the initial request is unable to be resolved, the request may be flagged and/or sent for review by, for example, a nurse practitioner. During the review, a nurse practitioner may evaluate the request and provide approvals for treatments within clinical guidelines. For procedures that fall outside of these criteria, the nurse practitioner may discuss an alternative care pathway. If consensus is not reached, the request may be further escalated for a peer-to-peer consultation. During a peer-to-peer consultation, a physician may review the treatment. After consultation with the requesting provider, the procedure may be approved, or the provider may agree to perform a different procedure or no procedure. If agreement is not reached with the provider, coverage may be denied.

However, initial review and subsequent peer-to-peer consultation—i.e., the "off-ramping" decision process that may initiate from the software solution but ultimately requires further consideration—can be time consuming. Time and resources devoted to those reviews could be more efficiently used to treat patients.

SUMMARY OF THE INVENTION

The present invention is directed to improved systems and methods for off-ramping automated decision processing engines. A machine learning algorithm may be used to review and approve requested procedures that are initially flagged for denial by the processing engine, but which are similar to procedures that have been approved historically.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIG. 5 depicts an exemplary user interface in accordance with the present invention;

FIG. 6 depicts an exemplary user interface in accordance with the present invention;

FIG. 9 depicts an exemplary user interface in accordance with the present invention;

FIG. 13 depicts an exemplary user interface in accordance with the present invention.

DETAILED DESCRIPTION OF THE INVENTION

The invention may be understood by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It must be noted that, as used in the specification and the appended claims, the singular forms "a", "an", and "the" include plural referents unless the context clearly indicates otherwise.

The present invention is directed to an improved medical protocol driven procedure assessment engine. The new assessment engine may be designed to take into account (1) pass rate requirements for rules; (2) weighted averages of criteria within a rule; and/or (3) iterative rule processing (i.e., branching). Rules may be built based on medical protocols configured based on diagnosis (DX) codes. Each DX may have a set of rules pre-configured.

Protocols and Decision Nodes

Figure 1:
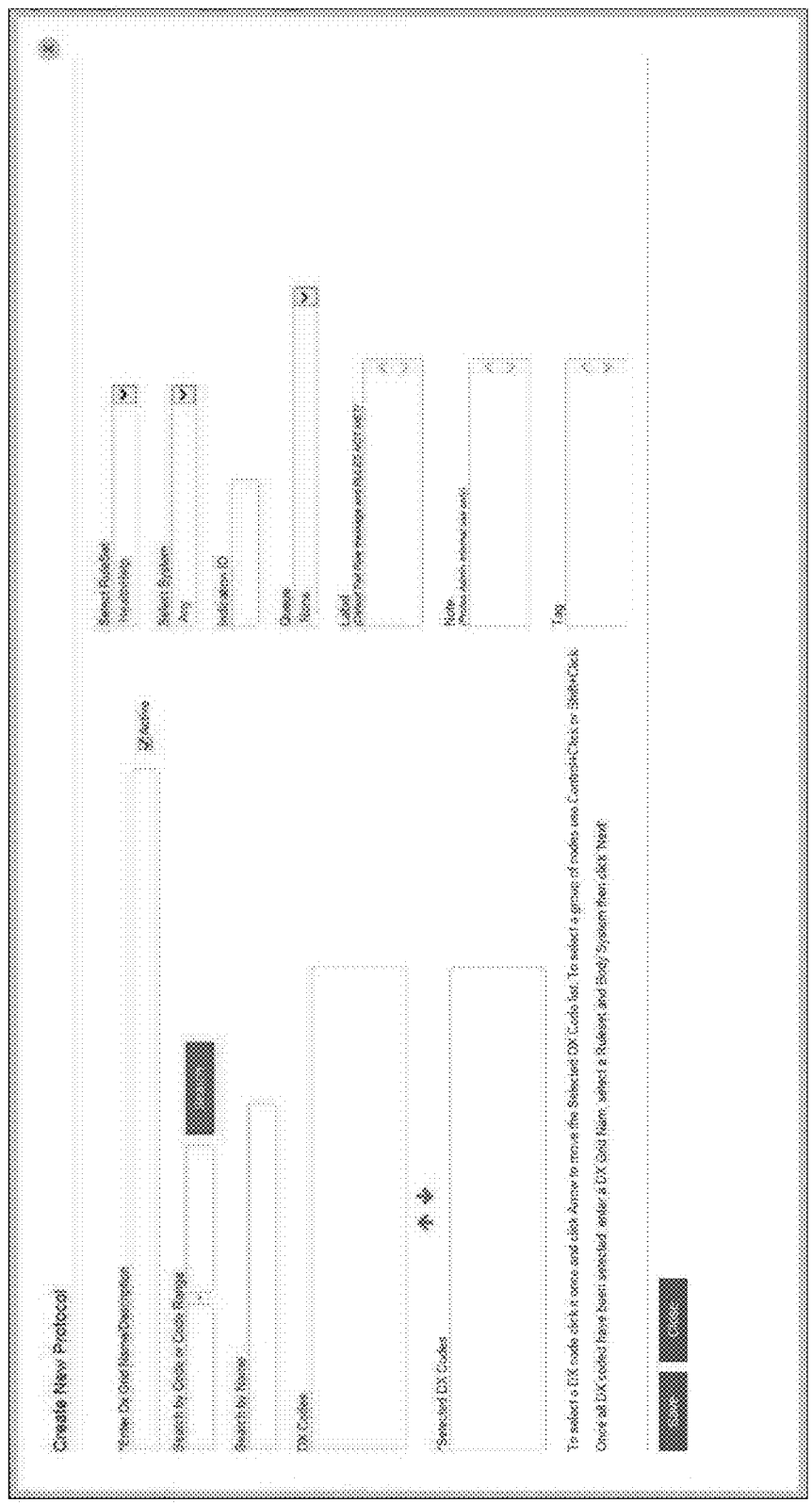
FIG. 1 depicts an exemplary user interface in accordance with the present invention.

Each protocol may be established with multiple decision nodes, and one or more DX codes may be selected for each protocol. Each decision node may consist of clinical conditions and clinical criteria. The user interface shown in FIG. 1 is an example of an interface that may be used to create a new DX protocol. The user may enter a name or description for the Protocol. The user may then select DX codes. DX codes may be searched by code or code range, or by using type ahead in a search-by-name box.

Figure 2:
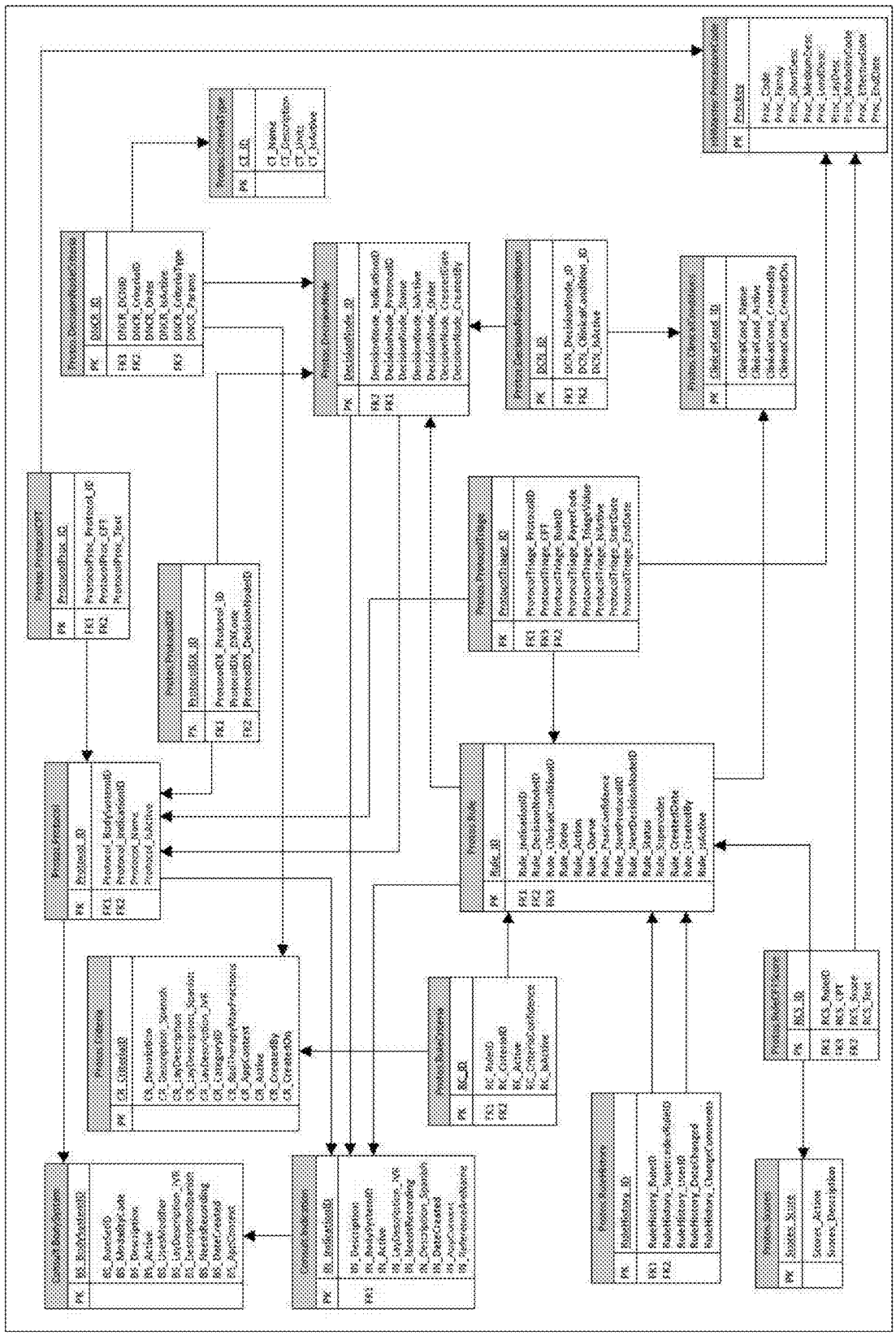
FIG. 2 depicts an exemplary database map in accordance with the present invention.

The user may add decision nodes (decision branches) to the protocol. Each decision node may consist of clinical conditions, rules, clinical criteria, procedure codes/scores, and/or triage. Once a decision node has been added, it may be edited, moved, or removed. The elements of the procedure assessment engine (e.g., protocols, decision nodes, clinical conditions, rules, clinical criteria) may be established and saved as a series of database tables. FIG. 2 shows an example databases map—including exemplary databases and database fields—that may be used to generate and practice a procedure assessment engine in accordance with the present invention.

Clinical Conditions

Figure 3:
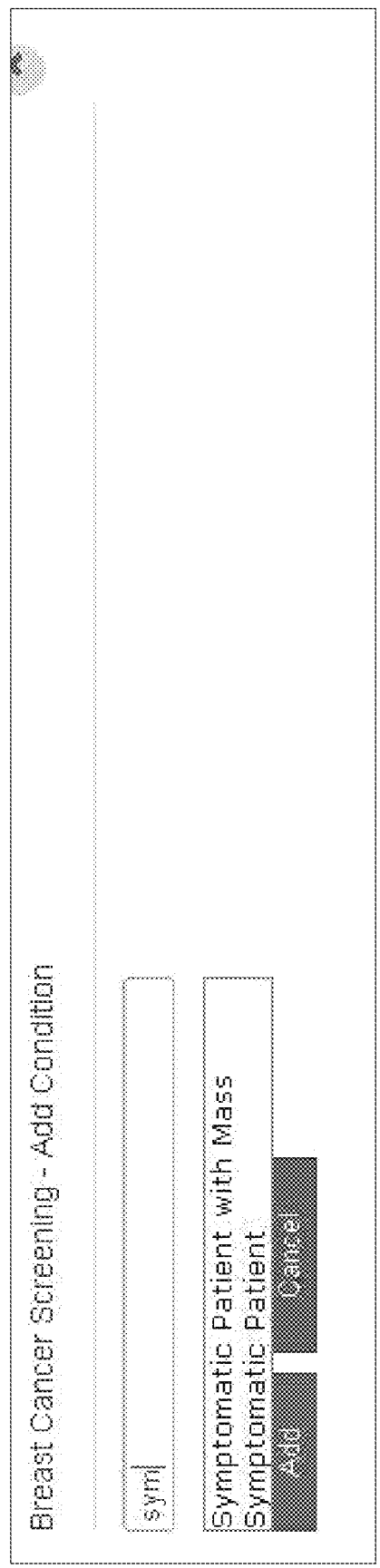
FIG. 3 depicts an exemplary user interface in accordance with the present invention.

The user interface shown in FIG. 3 is an example interface that may be used to add clinical conditions to a decision node. The user may be presented, for example, with a drop-down list of existing clinical conditions. In the alternative, the user may type the name of a clinical condition and the interface may display a type-ahead list from which a clinical condition may be selected. In the alternative, the user may simply type the name of a new clinical condition. In a preferred embodiment, the condition name is unique to the decision node. If the user types in a condition already found in the decision node, an error message may be displayed.

Rules

Figure 4:
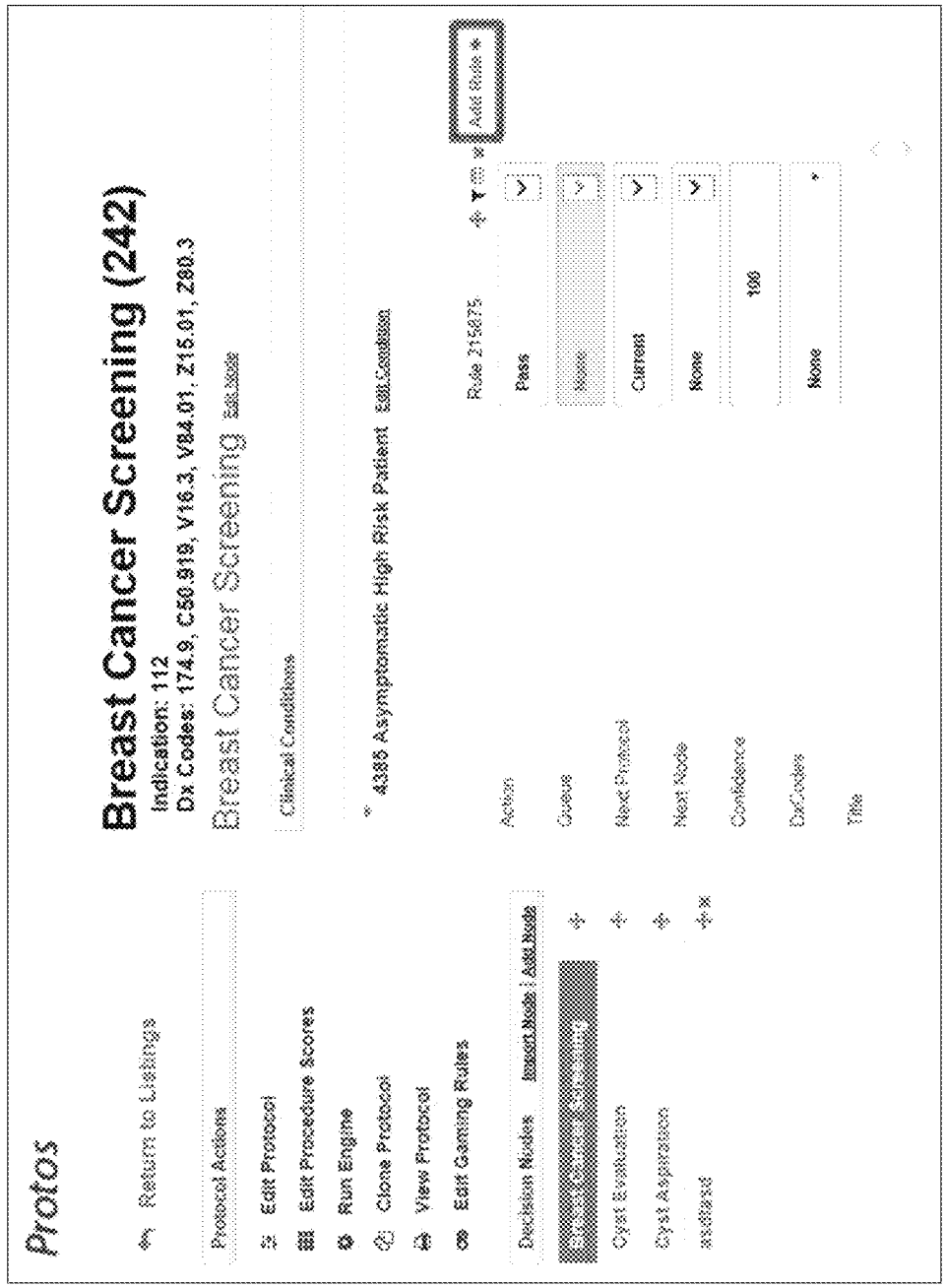
FIG. 4 depicts an exemplary user interface in accordance with the present invention.

The user interfaces shown in FIGS. 4 and 5 are example interfaces that may be used to add rules to clinical conditions. In FIG. 4, the user may select "Add Rule" to add a rule. The system may then display the interface shown in FIG. 5, which may be used to enter information about the rule. When adding a new rule, the user may enter (or be required to enter) one or more of the following: (1) an action (pass or fail), (2) an indication to be associated with the requested procedure or a queue to which the case may be escalated if the rule is failed, (3) a next protocol, (4) a next node, and/or (5) a confidence threshold number. The user may also be able to enter an order number which would be used to determine the order in which the rules are processed. When the procedure assessment engine is run, it may present the rules in order (e.g. ascending or descending) according to the order numbers assigned to each rule.

In a preferred embodiment, every rule is assigned an "action." The "action" determines whether the rule is a "Pass Rule" or "Fail Rule." The user interface may present to the user a drop-down menu with the option of "Pass" or "Fail." When the procedure assessment engine is run, if a Pass Rule, is met the procedure assessment engine may approve the requested procedure. In addition or in the alternative, the user may be presented with a list of approved procedures, one of which may be the procedure originally proposed by the user. If a Pass Rule is not met, the procedure assessment engine may proceed to the next rule. If a Fail Rule is met, the procedure assessment engine may deny the requested procedure. In a preferred embodiment, a procedure may be approved if at least one Pass Rule is met, and no Fail Rules are met.

Figure 6:
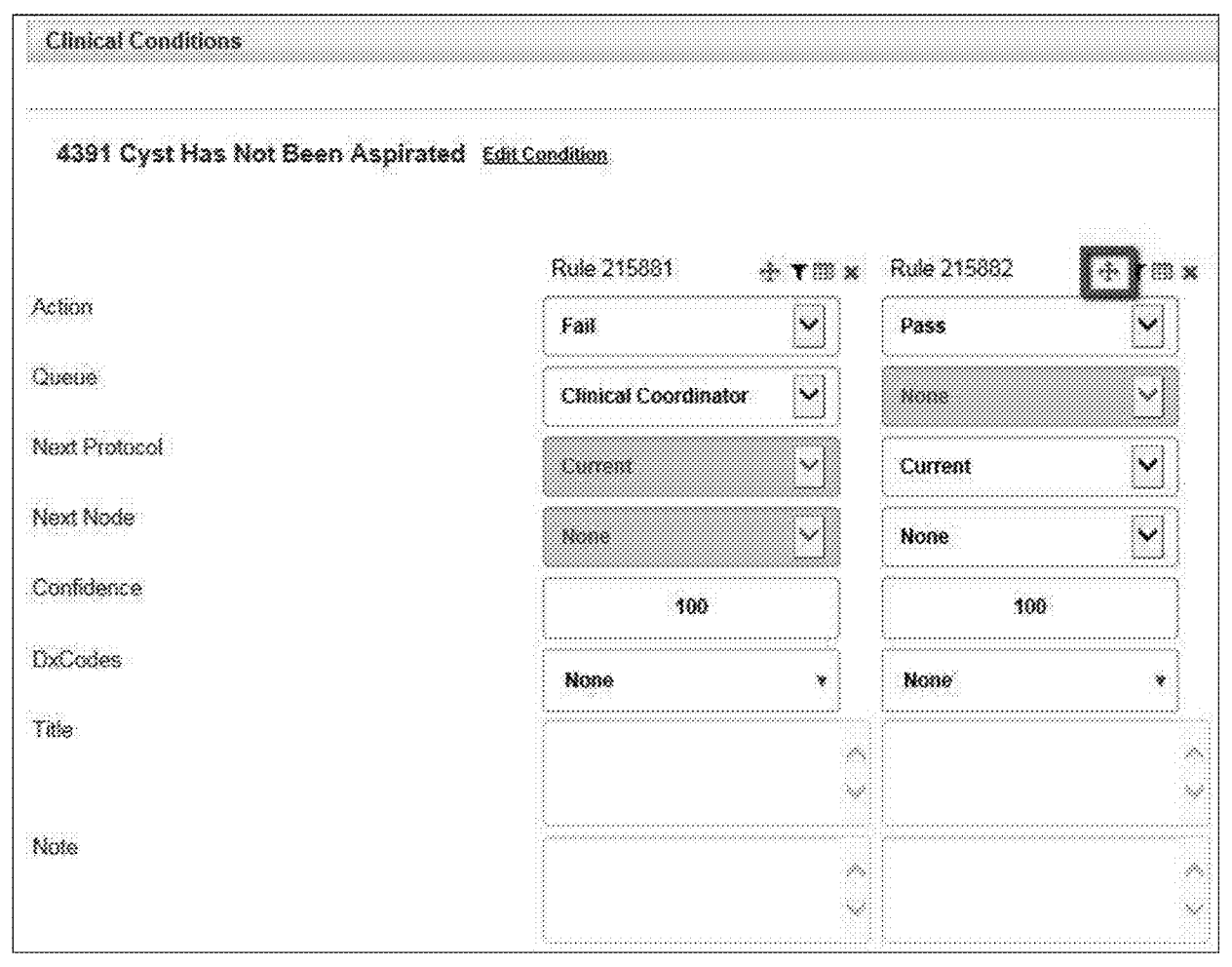

FIG. 6 depicts an example user interface showing two exemplary rules, Rules 215881 and 215882. In a preferred embodiment, each rule is assigned a unique ID. Rule 215881 is an example of a Fail Rule and Rule 215882 is an example of a Pass Rule. Fail Rules may specify a queue to which a requested procedure may be assigned if the Fail Rule is met. As shown in FIG. 6, if Rule 215881 is failed, the case would be assigned to a Clinical Coordinator.

Also as shown in FIG. 6, each rule may have a confidence value. The confidence threshold number may be any number and determines the total of the clinical criteria values that must be met in order for the rule to be met (pass or fail). Each clinical criteria associated with a rule is given a value and the total of those values must be greater than the confidence threshold number for the rule to be met.

The "next protocol" and "next node" fields determine whether the user will have to proceed to another protocol or another node if a Pass Rule is met.

Figure 7:
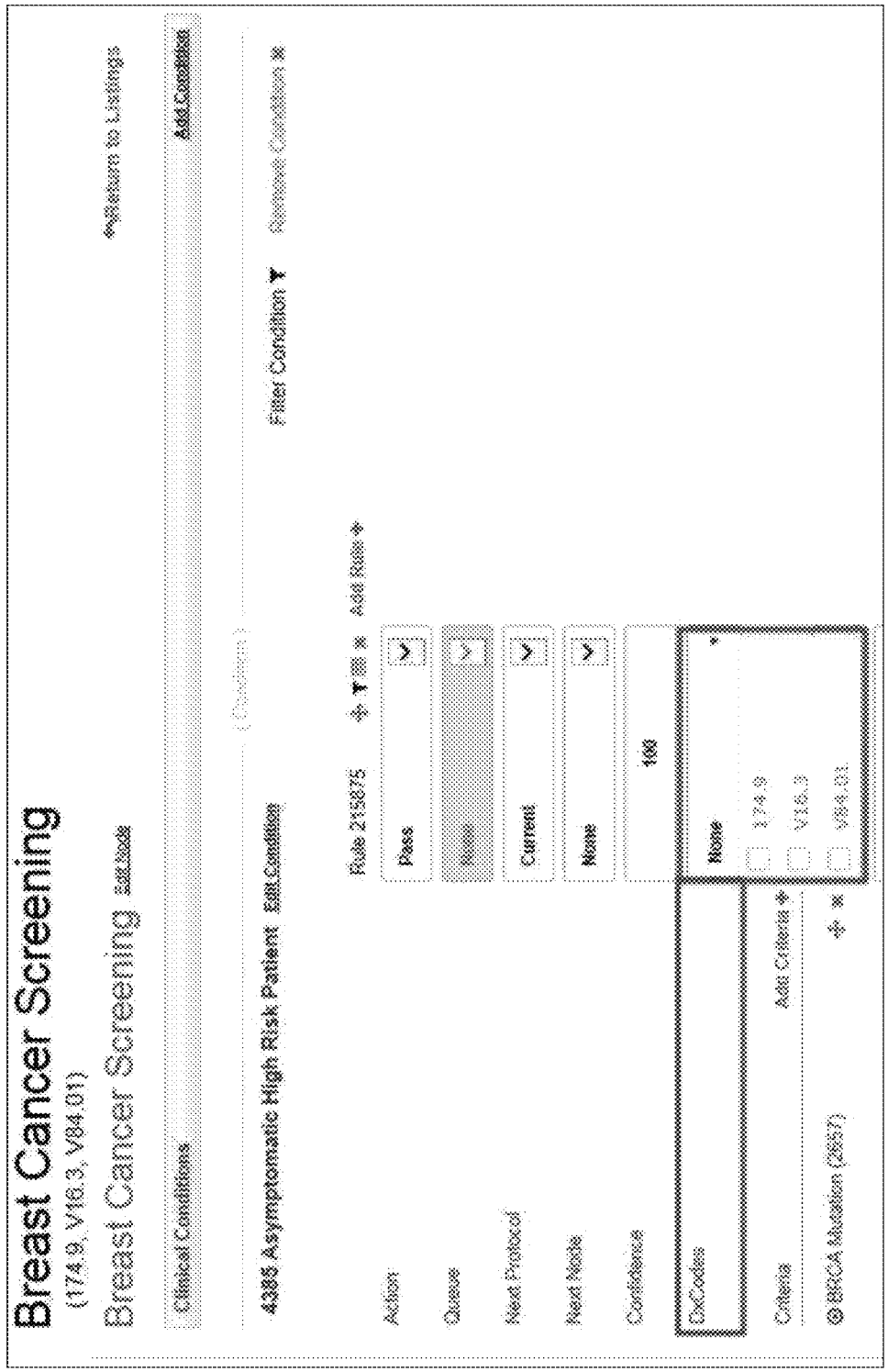
FIG. 7 depicts an exemplary user interface in accordance with the present invention.

As shown in FIG. 7, once a rule has been added, a field for DX codes may be displayed. This field may allow the user to select one or more DX codes that would apply to the rule. The user may be presented with a drop-down menu that may display the full DX code list from the protocol. The list of DX codes may be displayed with checkboxes that allow one or more codes to be selected.

Clinical Criteria

Figure 8:
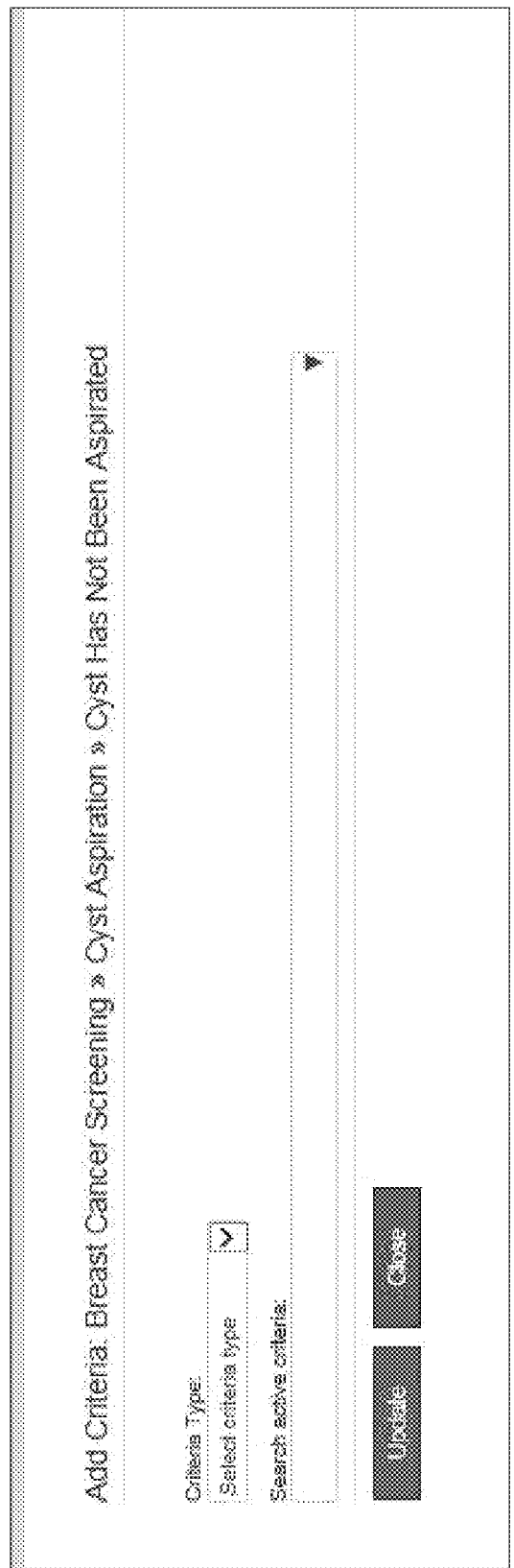
FIG. 8 depicts an exemplary user interface in accordance with the present invention.
Figure 9:
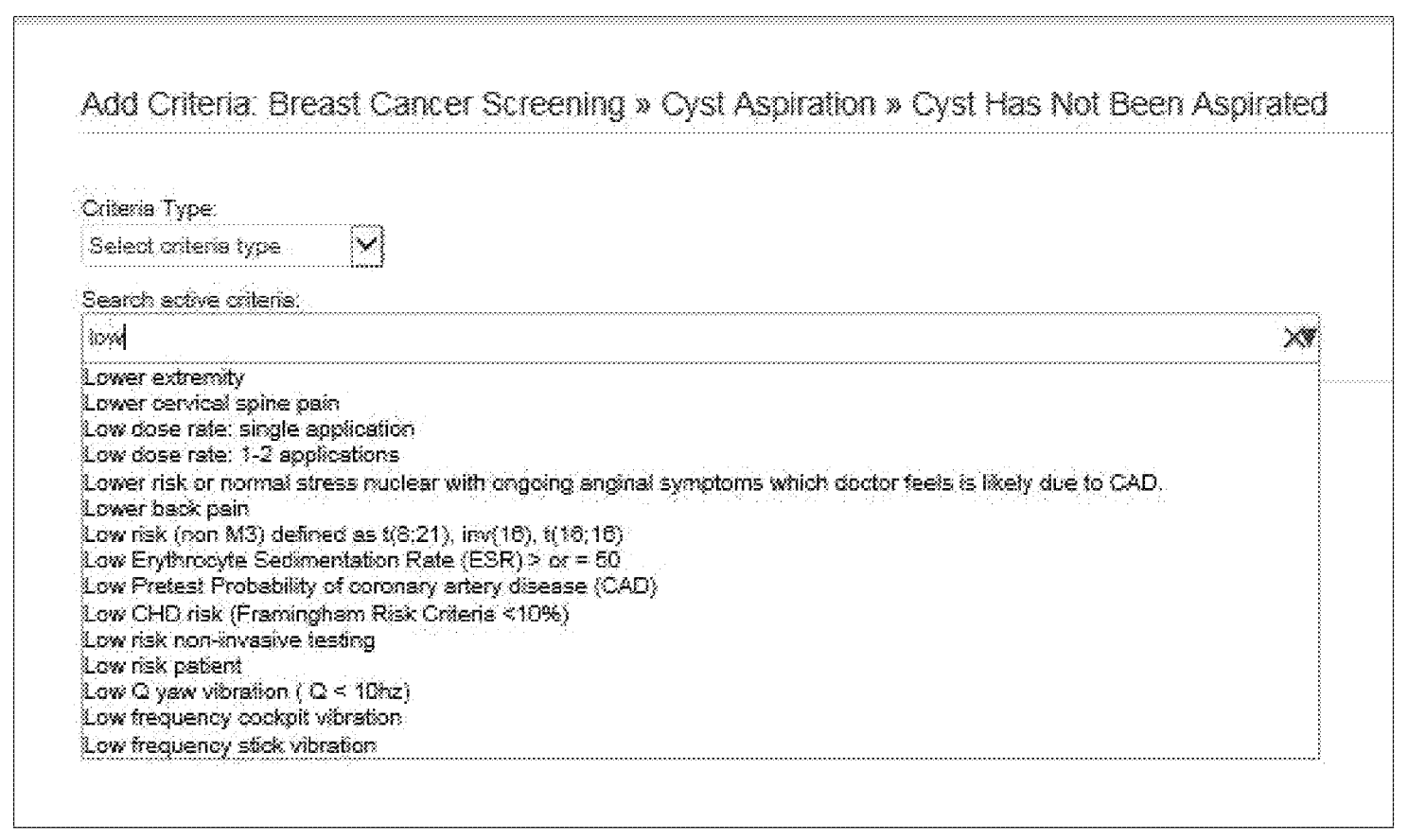
Figure 10:
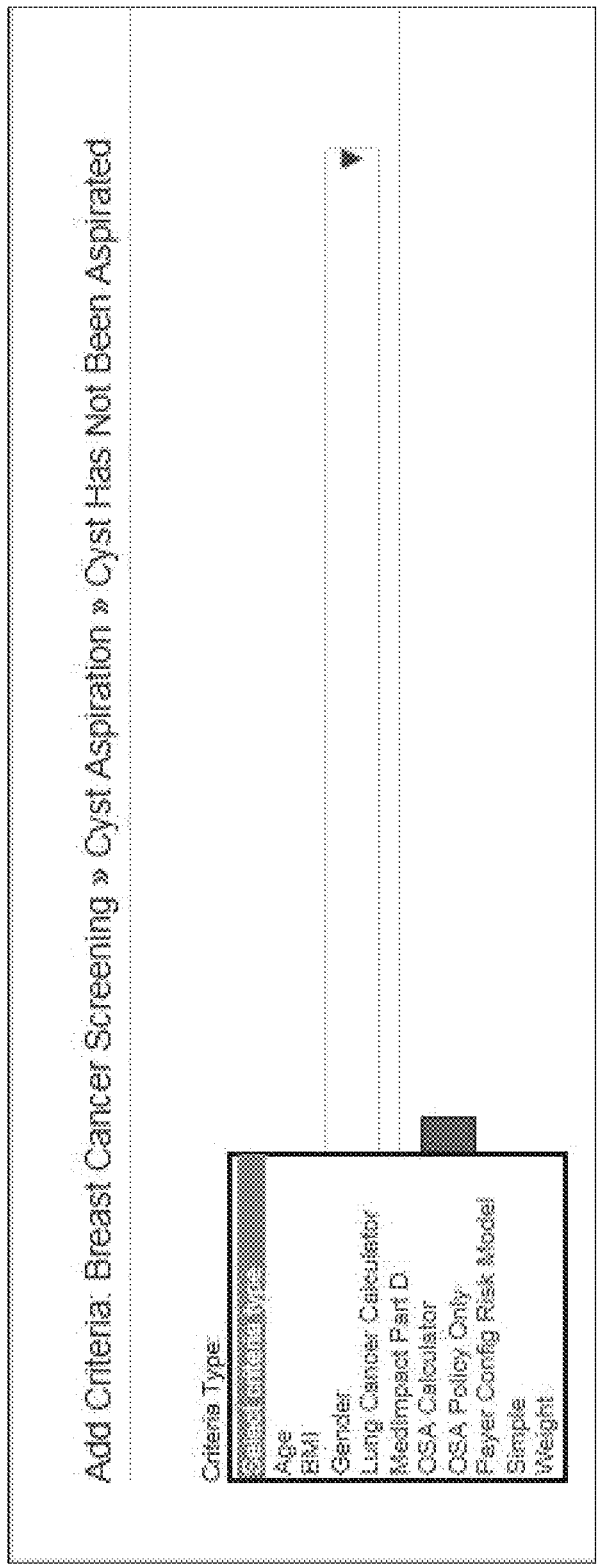
FIG. 10 depicts an exemplary user interface in accordance with the present invention.

A set of clinical criteria may be associated with each rule. Referring to FIGS. 8 and 9, to add new clinical criteria to a rule, the user can start typing in the criteria box and a type-ahead list will be displayed. The user can select an existing criteria from the list, or enter new criteria. Each criteria has a criteria type. The available criteria types may be displayed in a drop-down menu as shown, for example, in FIG. 10. Example criteria types are age, gender, weight, height, and body mass index (BMI). Certain criteria such as age, gender, weight, and height may be stored in the system or in another system which the procedure assessment engine may access. When the procedure assessment engine is run, it may retrieve such criteria. Certain criteria may be calculated based on other criteria values. For example, BMI may be determined from a patient's weight and height.

As described above, each clinical criteria may be assigned a confidence value. A value entered for a criteria may indicate to the system that the criteria should be shown for the clinical condition in the user interface when the procedure assessment engine in run. For each criteria selected, the confidence value of the criteria are added together. If the sum of the confidence values meets or exceeds the confidence threshold number assigned to a rule, then the rule is met (e.g., passed or failed). The confidence threshold number may be restricted to between 1 and 10, 1 and 100, or any other range. Dynamic criteria may also be used, for example: $male$ or $age>50$.

For the system to determine if the requested procedure is the best procedure, the rules may also consist of procedure codes and scores. This information may be used to show the user the results page and offer alternative procedures based on the score.

Figure 11:
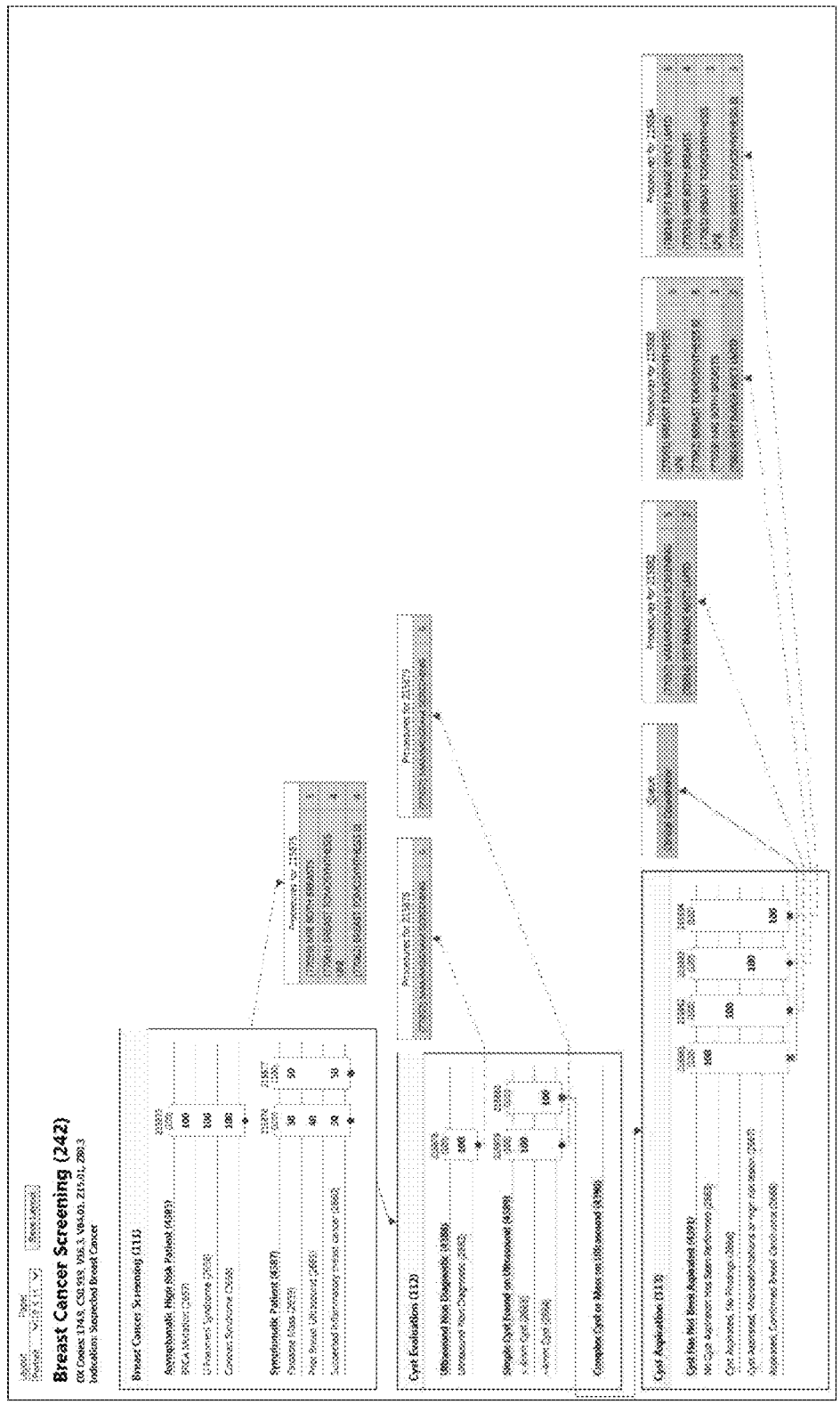
FIG. 11 depicts an exemplary tree view of a protocol.

As shown in FIG. 11, each protocol may be viewed as a tree view. The tree view may show the protocol, decision nodes, and clinical conditions.

Figure 12:
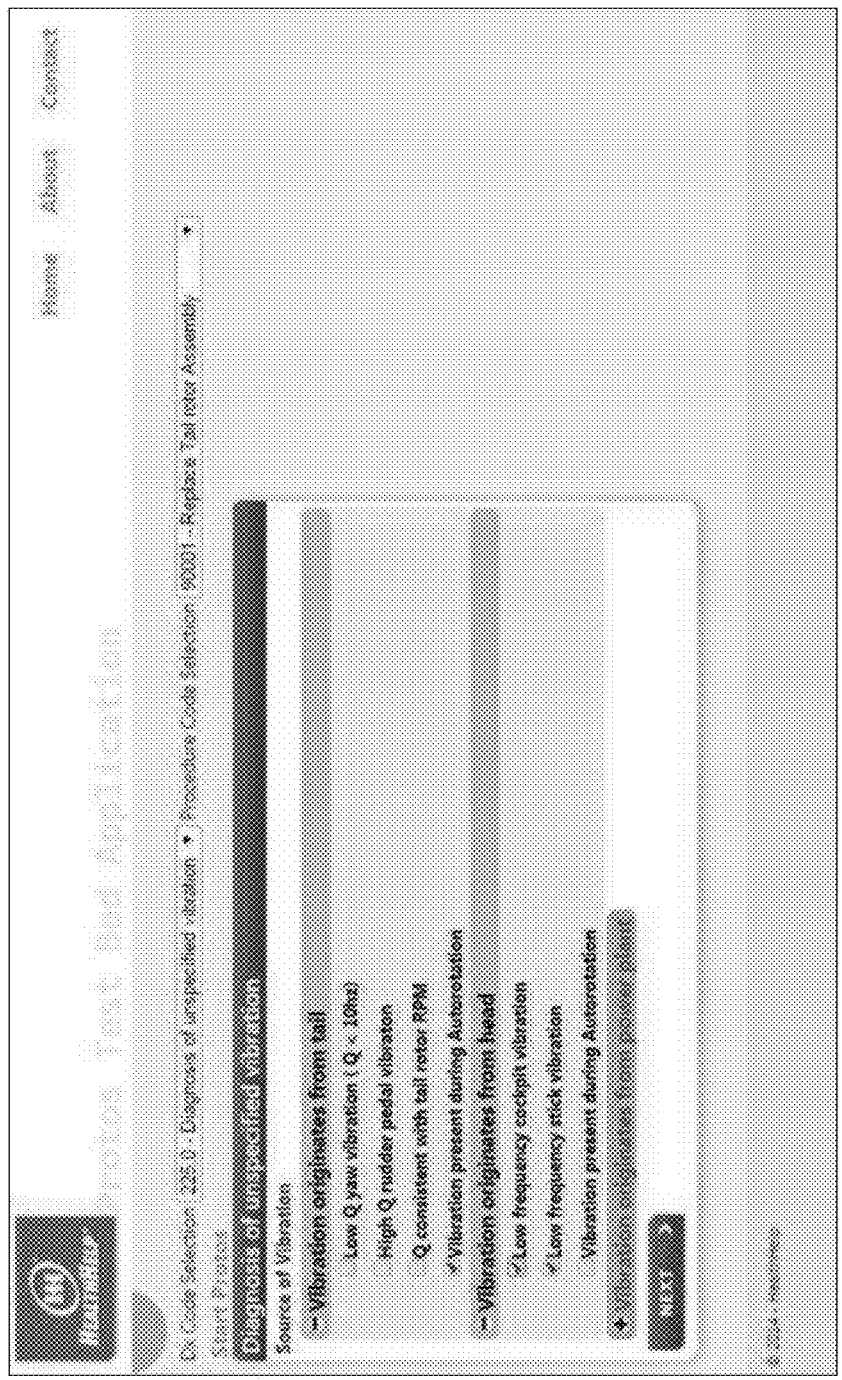
FIG. 12 depicts an exemplary user interface in accordance with the present invention.

Although a procedure assessment engine is described herein as used to assess proposed medical procedures, the assessment engine may also be used in other contexts. Referring to FIG. 12, a user interface is shown for a procedure assessment engine that may be used for aircraft repair. Two conditions are shown: (1) "Vibration originates from tail"; and (2) "Vibration originates from head." Three criteria are associated with each condition, and the rules for each condition may require all three criteria to be met. The criteria "Vibration present during Autorotation" is associated with both conditions. Since the criteria "Vibration present during Autorotation" is selected in the first condition (Vibration originates from tail), the same criteria may also be determined as met for the second condition "Vibration originates from head," even if it is not selected for the second condition.

Analyzing Rules and Results

A variable that may be taken into consideration when processing the rules and presenting the results may be the user status. For example, if the user of the assessment engine is identified as a physician, the results of the assessment may be presented as a score and the user may be offered choices to change the requested procedure. As another example, if the user of the assessment engine is identified as a clerk, the assessment engine may indicate whether the requested procedure is approved and may present alternatives in simple terms. A clerk may also be presented with a message based on a CPT/DX.

When the procedure assessment engine is run, after the rules have been analyzed, the user may be presented with a results screen. An example of a results screen is shown in FIG. 13. The user may be provided with a list of alternative procedures. The list may be sorted according to score (e.g., descending) or cost (e.g., ascending). The score and/or cost may be shown on the results screen.

If the original requested procedure is denied but one or more alternative procedures are presented to the user, the user may select an alternative procedure. The alternative procedure may then be substituted for the original requested procedure and approved immediately. Alternatively, the user may provide an input to the assessment engine indicating that the user is withdrawing the request. Alternatively, the user may provide an input to the system indicating that the user chooses to maintain the original request.

If the user maintains the original request, the request may be forwarded to a review queue for review by, for example, a nurse practitioner or for peer-to-peer consultation. In the alternative, the request may be evaluated using a machine learning algorithm. The machine learning algorithm may be a neural network. The machine learning algorithm may output a score representing the probability that the request procedure is necessary. The score can be compared to a threshold score to determine whether the procedure should be approved. An indication of whether the procedure is approved may be displayed as described above. As described above, if a procedure is not approved, alternative procedures may be suggested.

The data input to the machine learning algorithm may include (1) clinical criteria; (2) medical data for a patient; (3) one or more diagnosis codes; and/or (4) information concerning whether the same procedure requested for patients with similar medical data and/or similar clinical criteria was approved. The medical data may include, for example, the patient's age, gender, weight, and/or height, the number of times the procedure has been previously administered to the patient, and the amount of time that has passed since the requested procedure was last administered to the patient. Other data input to the machine learning algorithm may include data indicating the percentage of times that the procedure has been approved when forwarded to a particular review queue.

The output from the machine learning algorithm may be monitored and the system may further receive data concerning whether each output score should have been higher or lower. As additional requests and data are assessed by the machine learning algorithm, the algorithm may change over time. For diagnostic purposes, or in case a decision whether to approve a procedure is challenged, a system in accordance with the present invention may periodically save the machine learning algorithm. For example, the machine learning algorithm may be saved every day. In addition or in the alternative, the machine learning algorithm may be saved immediately before or immediately after every assessment. The machine learning algorithm may be saved on computer storage medium so that the state of the machine learning algorithm at any point in time may be retrieved at a later time, after further assessments are performed. In other words, the system may perform the following steps: (1) save the machine learning algorithm in a first state; (2) receive a selection of a second set of one or more clinical criteria; (3) determine whether the sum of the confidence values associated with the second set of one or more clinical criteria exceed a confidence threshold number; (4) in response to the determination of whether the sum of the confidence values associated with the second set of one or more clinical criteria exceed the confidence threshold number, use the machine learning algorithm to generate an output indicating whether a second medical procedure should be approved, wherein the machine learning algorithm changes from the first state to a second state; and (5) after generating the output indicating whether the second medical procedure should be approved, retrieving the machine learning algorithm in the first state.

In addition or in the alternative, a system or method in accordance with the present invention may include an algorithm that may be used to determine whether a rule is blocked. A first rule may be blocked if it is associated with the same criteria as a second rule plus one or more additional criteria that are not associated with the second rule. In that instance, the first rule may never be considered. A rule also may be blocked if two associated criteria are contradictory.

The present invention includes a computer readable medium having program code recorded thereon, for execution on a computer having a graphical user interface and a user input device, said program code configured to generate or modify a protocol hierarchy according to a method comprising: receiving a request to create a decision node of the protocol hierarchy; entering in a first database table a first record representing the requested decision node; receiving a request to associate a condition with the decision node; entering in a second database table a second record representing the condition and an association between the condition and the decision node; receiving a request to associate a plurality of rules with the condition; entering in a third database table a plurality of rule records, wherein each rule record represents a rule and an association between the rule and the condition; receiving a request to associate a plurality of criteria with a rule; entering in a fourth database table a plurality of criteria records, wherein each criteria record represents a criterion and an association between the criterion and a rule; upon entering a first criteria record in the fourth database table, determining whether the rule associated with the criterion in the first criteria record is blocked; upon determining that a rule is blocked, presenting on the graphical user interface a first graphical element representing the option to delete a criteria record, and a second graphical element representing the option to edit a criteria record; receiving an input corresponding to selection of one of the first graphical element or the second graphical element; wherein if an input corresponding to selection of the second graphical element is received, presenting on the graphical user interface data from the first criteria record.

The present invention further includes systems and methods for assessing whether one or more medical procedures should be approved, such as a computer memory having a machine-readable medium comprising machine-executable code recorded thereon, said machine-executable code comprising instructions for: (1) entering in a first database table a first record wherein said first record represents a first rule and wherein said first record comprises a confidence threshold number; (2) entering in a second database table one or more records wherein each record represents a clinical criterion and wherein each record comprises a confidence value associated with the clinical criterion; (3) receiving a selection of a first set of one or more clinical criteria; (4) determining whether the sum of the confidence values associated with the first set of one or more clinical criteria exceed the confidence threshold number; (5) in response to the determination of whether the sum of the confidence values associated with the first set of one or more clinical criteria exceed the confidence threshold number, receiving medical data and processing the medical data and the first set of one or more clinical criteria using a first machine learning algorithm to generate an output indicating whether the medical procedure should be approved; (6) displaying on a computer screen an indication of whether the procedure is approved.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for assessing whether one or more medical procedures should be approved, comprising:
   a computer memory having a non-transitory machine-readable medium comprising machine-executable code recorded thereon, said machine-executable code comprising instructions for:
      entering in a first database table a first record wherein said first record represents a first rule and wherein said first record comprises a confidence threshold number;
      entering in a second database table one or more records wherein each record represents a clinical criterion and wherein each record comprises a confidence value associated with the clinical criterion;
      receiving a selection of a first set of one or more clinical criteria;
      determining whether the sum of the confidence values associated with the first set of one or more clinical criteria exceed the confidence threshold number;
      in response to the determination of whether the sum of the confidence values associated with the first set of one or more clinical criteria exceed the confidence threshold number, receiving medical data and processing the medical data and the first set of one or more clinical criteria using a first machine learning algorithm to generate a first output indicating whether a first medical procedure should be approved;
      after generating the first output, saving a first state of the machine learning algorithm;
      displaying on a computer screen an indication of whether the procedure is approved;
      receiving a selection of a second set of one or more clinical criteria;
      determining whether the sum of the confidence values associated with the second set of one or more clinical criteria exceed the confidence threshold number;
      in response to the determination of whether the sum of the confidence values associated with the second set of one or more clinical criteria exceed the confidence threshold number, using the machine learning algorithm to generate a second output indicating whether a second medical procedure should be approved, wherein the machine learning algorithm is converted from the first state to a second state;
      after generating the second output indicating whether the second medical procedure should be approved, saving the second state of the machine learning algorithm and retrieving the first state of the machine learning algorithm; and
      after retrieving the first state of the machine learning algorithm, receiving a selection of a third set of one or more clinical criteria, determining whether the sum of the confidence values associated with the clinical criteria exceed the confidence threshold number, and using the machine learning algorithm in the second state to generate a third output indicating whether a second medical procedure should be approved.

2. The system of claim 1, wherein the machine-executable code further comprises instructions for displaying on the computer screen one or more alternative procedures.

3. The system of claim 2, wherein the medical data comprises one or more selected from the group consisting of a patient's age, a patient's gender, a patient's weight, a patient's height, and the number of times the procedure has been previously administered.

4. The system of claim 2, wherein the machine learning algorithm is a neural network.

5. The system of claim 4, wherein the medical data comprises one or more selected from the group consisting of a patient's age, a patient's gender, a patient's weight, a patient's height, and the number of times the procedure has been previously administered.

6. The system of claim 1, wherein the medical data comprises one or more selected from the group consisting of a patient's age, a patient's gender, a patient's weight, a patient's height, and the number of times the procedure has been previously administered.

7. The system of claim 6, wherein the machine learning algorithm is a neural network.

8. The system of claim 1, wherein the machine learning algorithm is a neural network.

9. A method for assessing whether one or more medical procedures should be approved, comprising:
 entering in a first database table a first record wherein said first record represents a first rule and wherein said first record comprises a confidence threshold number;
 entering in a second database table one or more records wherein each record represents a clinical criterion and wherein each record comprises a confidence value associated with the clinical criterion;
 receiving a selection of a first set of one or more clinical criteria;
 determining whether the sum of the confidence values associated with the first set of one or more clinical criteria exceed the confidence threshold number;
 in response to the determination of whether the sum of the confidence values associated with the first set of one or more clinical criteria exceed the confidence threshold number, receiving medical data and processing the medical data and the first set of one or more clinical criteria using a first machine learning algorithm to generate a first output indicating whether a first medical procedure should be approved;
 after generating the first output, saving a first state of the machine learning algorithm;
 displaying on a computer screen an indication of whether the procedure is approved;
 receiving a selection of a second set of one or more clinical criteria;
 determining whether the sum of the confidence values associated with the second set of one or more clinical criteria exceed the confidence threshold number;
 in response to the determination of whether the sum of the confidence values associated with the second set of one or more clinical criteria exceed the confidence threshold number, using the machine learning algorithm to generate a second output indicating whether a second medical procedure should be approved, wherein the machine learning algorithm is converted from the first state to a second state;
 after generating the second output indicating whether the second medical procedure should be approved, saving the second state of the machine learning algorithm and retrieving the first state of the machine learning algorithm; and
 after retrieving the first state of the machine learning algorithm, receiving a selection of a third set of one or more clinical criteria, determining whether the sum of the confidence values associated with the clinical criteria exceed the confidence threshold number, and using the machine learning algorithm in the second state to generate a third output indicating whether a second medical procedure should be approved.

10. The method of claim 9, further comprising displaying on the computer screen one or more alternative procedures.

11. The method of claim 10, wherein the medical data comprises one or more selected from the group consisting of a patient's age, a patient's gender, a patient's weight, a patient's height, and the number of times the procedure has been previously administered.

12. The method of claim 10, wherein the machine learning algorithm is a neural network.

13. The method of claim 12, wherein the medical data comprises one or more selected from the group consisting of a patient's age, a patient's gender, a patient's weight, a patient's height, and the number of times the procedure has been previously administered.

14. The method of claim 9, wherein the medical data comprises one or more selected from the group consisting of a patient's age, a patient's gender, a patient's weight, a patient's height, and the number of times the procedure has been previously administered.

15. The method of claim 14, wherein the machine learning algorithm is a neural network.

16. The method of claim 9, wherein the machine learning algorithm is a neural network.

17. A system for assessing whether one or more medical procedures should be approved, comprising:
 a computer memory having a non-transitory machine-readable medium comprising machine-executable code recorded thereon, said machine-executable code comprising instructions for:
  entering in a first database table a first record wherein said first record represents a first rule and wherein said first record comprises a confidence threshold number;
  entering in a second database table one or more records wherein each record represents a clinical criterion and wherein each record comprises a confidence value associated with the clinical criterion;
  receiving a selection of a first set of one or more clinical criteria;
  determining whether the sum of the confidence values associated with the first set of one or more clinical criteria exceed the confidence threshold number;
  in response to the determination of whether the sum of the confidence values associated with the first set of one or more clinical criteria exceed the confidence threshold number, receiving medical data and processing the medical data and the first set of one or more clinical criteria using a first machine learning algorithm to generate a first output indicating whether a first medical procedure should be approved;
  after generating the first output, saving a first state of the machine learning algorithm;
  displaying on a computer screen an indication of whether the procedure is approved;
  receiving a selection of a second set of one or more clinical criteria;
  determining whether the sum of the confidence values associated with the second set of one or more clinical criteria exceed the confidence threshold number;

in response to the determination of whether the sum of the confidence values associated with the second set of one or more clinical criteria exceed the confidence threshold number, using the machine learning algorithm to generate a second output indicating whether a second medical procedure should be approved, wherein the machine learning algorithm is converted from the first state to a second state;

after generating the second output, saving the second state of the machine learning algorithm and retrieving the first state of the machine learning algorithm;

receiving a selection of a third set of one or more clinical criteria;

determining whether the sum of the confidence values associated with the third set of one or more clinical criteria exceed the confidence threshold number;

in response to the determination of whether the sum of the confidence values associated with the third set of one or more clinical criteria exceed the confidence threshold number, using the machine learning algorithm to generate a third output indicating whether a third medical procedure should be approved, wherein the machine learning algorithm is converted from the second state to a third state;

after generating the third output, retrieving the first state of the machine learning algorithm.

18. The system of claim 17, wherein the machine-executable code further comprises instructions for displaying on the computer screen one or more alternative procedures.

19. The system of claim 17, wherein the medical data comprises one or more selected from the group consisting of a patient's age, a patient's gender, a patient's weight, a patient's height, and the number of times the procedure has been previously administered.

20. The system of claim 17, wherein the machine learning algorithm is a neural network.

* * * * *